(12) United States Patent
Zbinden

(10) Patent No.: US 10,894,184 B2
(45) Date of Patent: Jan. 19, 2021

(54) FOOT STRETCHING DEVICE

(71) Applicant: Adam Zbinden, Portland, OR (US)

(72) Inventor: Adam Zbinden, Portland, OR (US)

( * ) Notice: Subject to any disclaimer, the term of this patent is extended or adjusted under 35 U.S.C. 154(b) by 107 days.

(21) Appl. No.: 16/428,983

(22) Filed: Jun. 1, 2019

(65) Prior Publication Data

US 2020/0009422 A1 Jan. 9, 2020

Related U.S. Application Data

(60) Provisional application No. 62/693,990, filed on Jul. 4, 2018.

(51) Int. Cl.
*A63B 23/10* (2006.01)
*A63B 23/08* (2006.01)
*A61F 5/01* (2006.01)

(52) U.S. Cl.
CPC .............. *A63B 23/08* (2013.01); *A61F 5/019* (2013.01); *A63B 23/10* (2013.01)

(58) Field of Classification Search
CPC ................................ A61F 5/019; A63B 23/10
USPC ........................................................ 602/30
See application file for complete search history.

(56) References Cited

U.S. PATENT DOCUMENTS

| | | | | |
|---|---|---|---|---|
| 5,076,263 A | * | 12/1991 | Funatogawa | A61F 5/019 602/30 |
| 6,629,943 B1 | * | 10/2003 | Schroder | A61F 5/019 602/30 |
| 7,131,939 B2 | * | 11/2006 | Ferri | A61F 5/10 482/148 |
| 7,676,850 B2 | * | 3/2010 | Steel | A43B 7/26 2/239 |
| 8,002,675 B2 | * | 8/2011 | Ferri | A61F 5/019 482/79 |

* cited by examiner

*Primary Examiner* — Joshua Kennedy

(57) ABSTRACT

A foot stretching device with simultaneous toe spacing and dorsiflexion capabilities, where the toe-spacing elements are continuously adjustable along flexible guiderails to custom fit individual foot geometry, while the method of applying tension between the ankle and the forefoot via inelastic material to enable dorsiflexion also secures the toe spacing elements to the user's foot through a linkage with the ankle cuff of the device. Exchanging the inelastic material for one which is elastic and stretchable allows plantarflexion exercises to be performed with resistance.

2 Claims, 5 Drawing Sheets

FOOT STRETCHING DEVICE

BACKGROUND OF THE INVENTION

Foot health problems, such as plantar fasciitis, can be alleviated by stretching the foot muscles to correct misalignments. Separating the toes with spacing implements placed in their gaps can therapeutically stretch the toes and improve foot muscle health.

Toe-spacers are an established method for performing this stretch. Toe-spacers insert rigid or flexible material between the toes at statically predetermined gaps and widths. This spacing causes an expansion of the toes and thereby stretches the muscles of the feet.

Dorsiflexion devices exert tension on the forefoot with an inelastic material which is anchored to the ankle or shin. Such a device stretches the plantar fascia and Achilles tendons by pulling the forefoot back toward the anchoring point, which is at a higher location on the leg, such that the angle between the heel and the forefoot is approximately perpendicular.

BRIEF SUMMARY OF THE INVENTION

Static toe-spacer effectiveness is limited by a lack of secure attachment mechanisms to the foot. Slight movements of the toes can cause the spacers to slide off the foot, resulting in a need for manual reinsertion and realignment. A method of securing the toe-spacers to the foot, after inserting them between the toes initially, is desirable.

An additional limitation of statically configured toe spacers is a lack of adjustability to individual foot sizes, as variation in foot geometry requires different spacing of the toe-separating-elements for each user. It is desirable to provide a means for separating the toes wherein the gaps between the toe-separating-elements can be continuously adjusted to the foot geometry of an individual user.

A key limitation of dorsiflexion devices is the covering of the forefoot, caused by the necessity of providing an anchoring point for the inelastic tensile element at this location. Such forefoot covering precludes the simultaneous use of static toe spacers, where simultaneous use would otherwise be desirable for optimal therapeutic stretching.

The aim of the present invention is to provide a means for stretching the foot muscles, using the combined methods of toe separation and dorsiflexion, where the following novel features address the above-noted limitations:
1) Continuously adjustable spacing elements can be placed in the natural toe-gaps of the user, where the spacing elements of the device are moveable along guiderails of the device via sliding action.
2) Inelastic straps of adjustable tension connect the toe-spacing elements and guiderails to a cuff which surrounds the lower leg, where the inelastic straps secure the adjustable toe-spacers to the foot such that the toe-spacers are not dislodged by natural toe or foot movements during use, while the adjustable inelastic connection also provides dorsiflexion by pulling the forefoot back toward the anchoring points located on the cuff which surrounds the lower leg.

Figure 1:
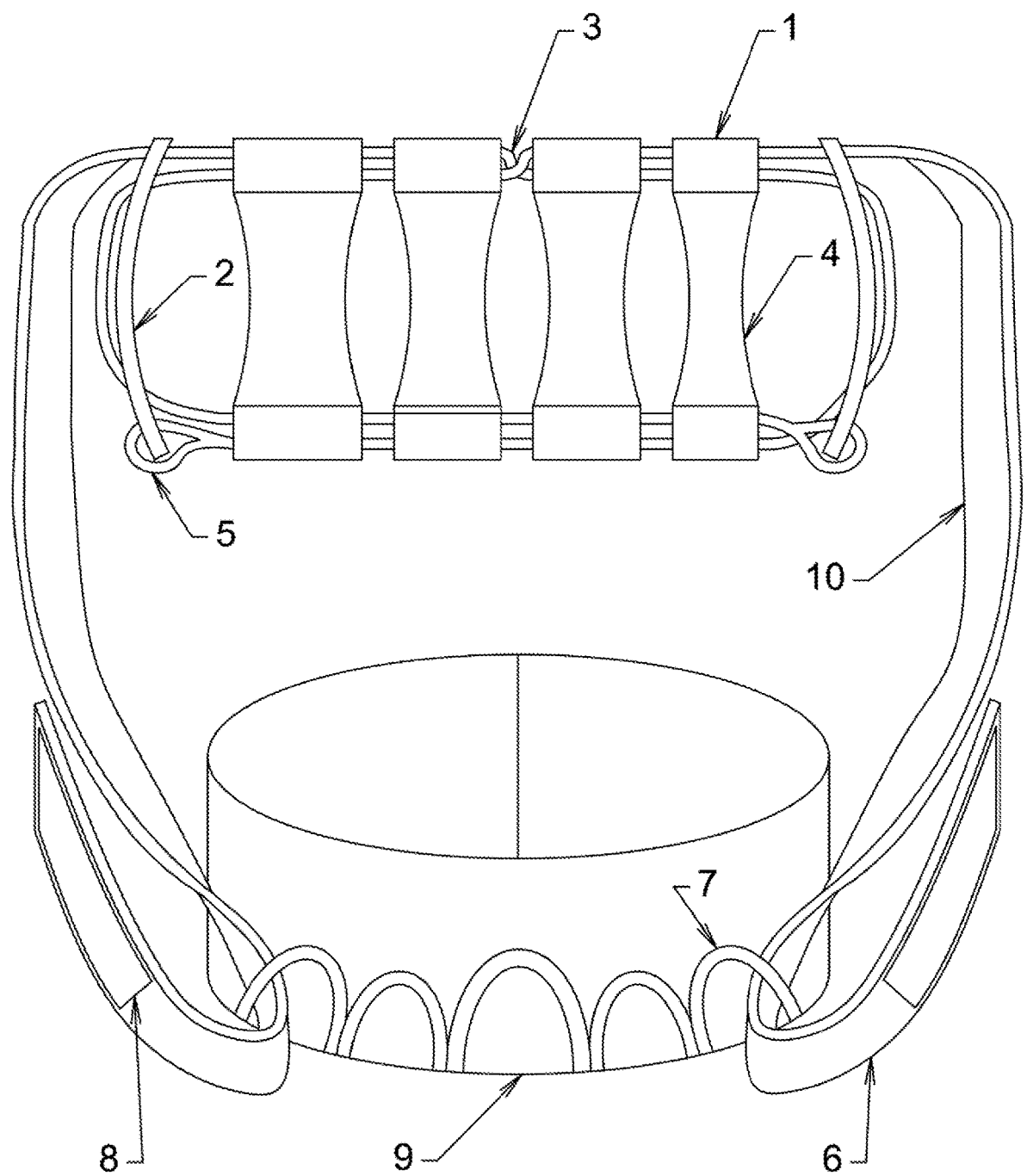
FIG. 1 is a depiction of the present invention, where the hollow connection slot is shown with (1) and is located at the endpoints of the inter toe spacing element (4). The flexible rail strap is shown with (3), which passes through (1) and links with (4). The anchored end of the flexible rail strap (3) is shown with (5) and is attached to the parabolic arc-shaped clasps at the extents of the forefoot, shown with (2). The travelling end of the flexible rail strap (3) is shown with (6) and is shown inserting through (2) after passing through (1). The ankle surrounding cuff is shown with (9), and its attachment surfaces are shown with (7). The inelastic tensile force linkage between the forefoot and lower leg is shown with (10) and is comprised of the linkage of the travelling end of the flexible rail strap (6) and attachment surfaces (7) which are connected to the cuff (9). A possible method for securing the connection between (6) and (7) is shown with (8) and represents hook and loop Velcro.
Figure 2:
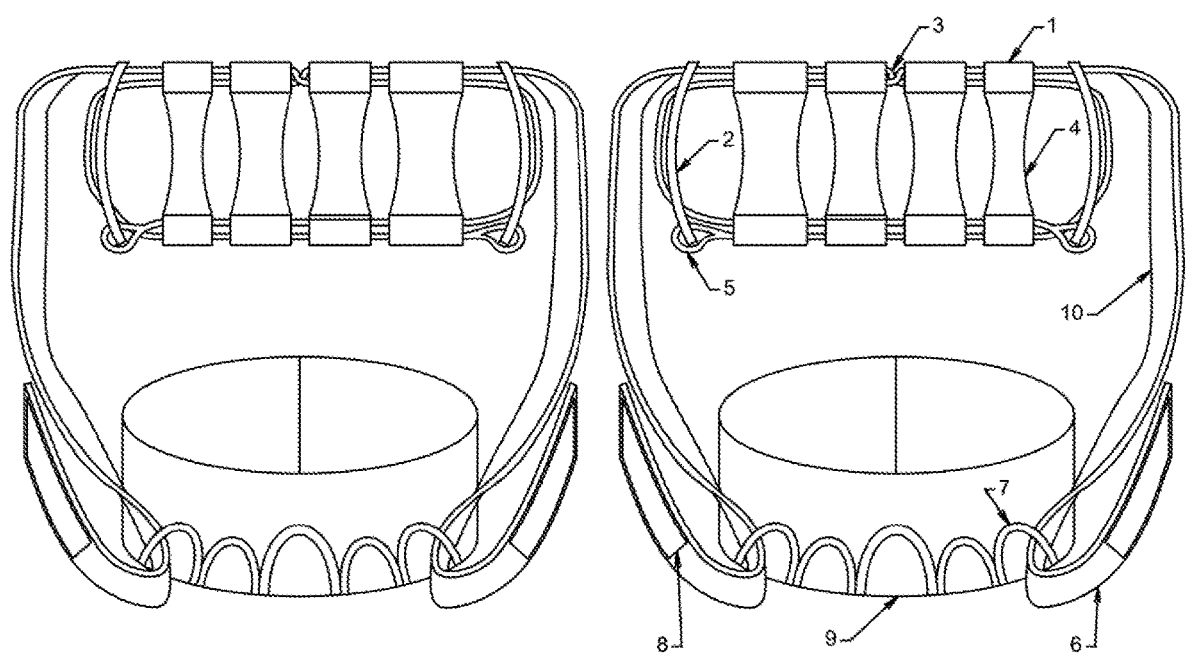
FIG. 2 is a front view of a pair of devices.
Figure 3:
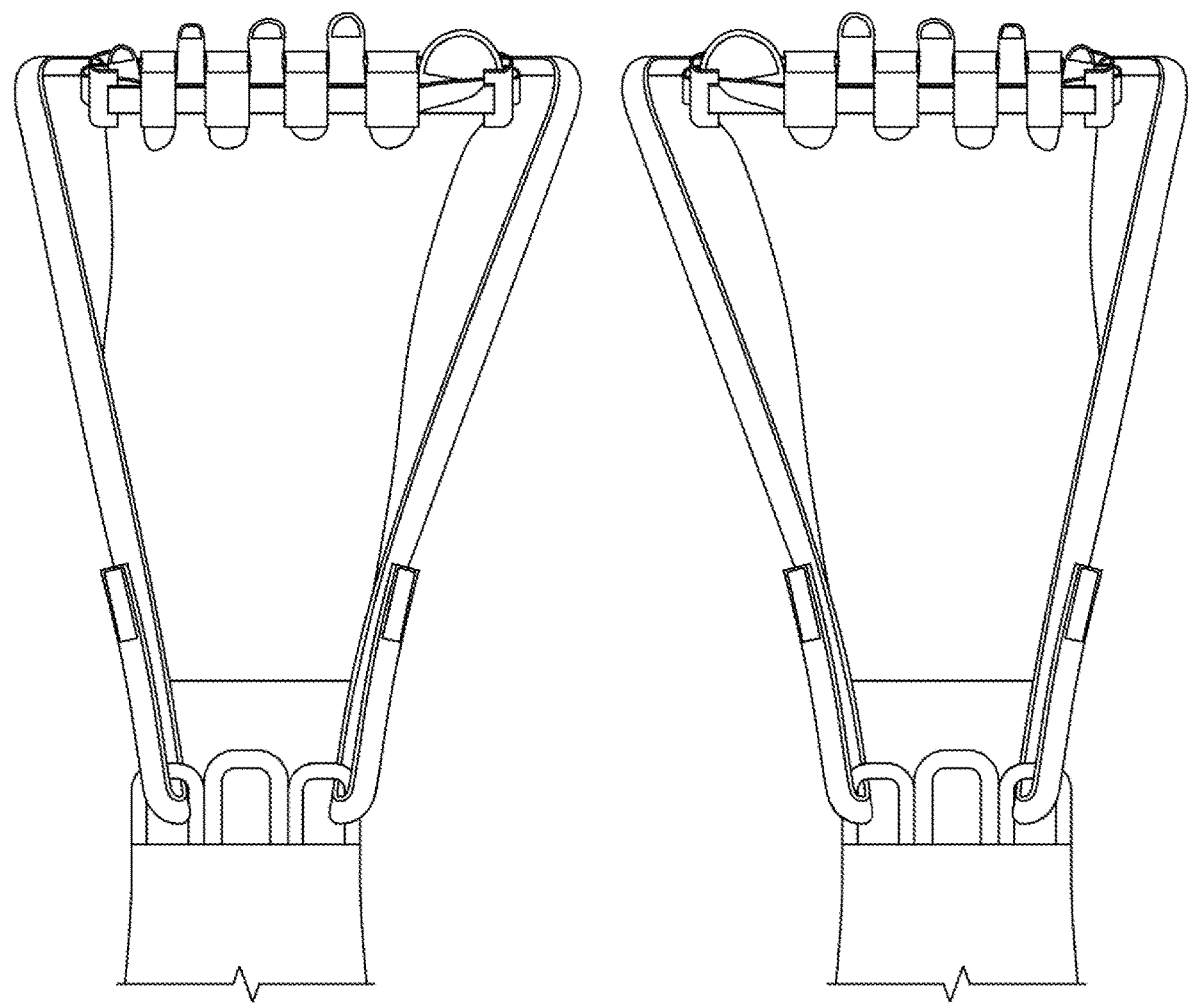
FIG. 3 is a depiction of the device when in use.
Figure 4:
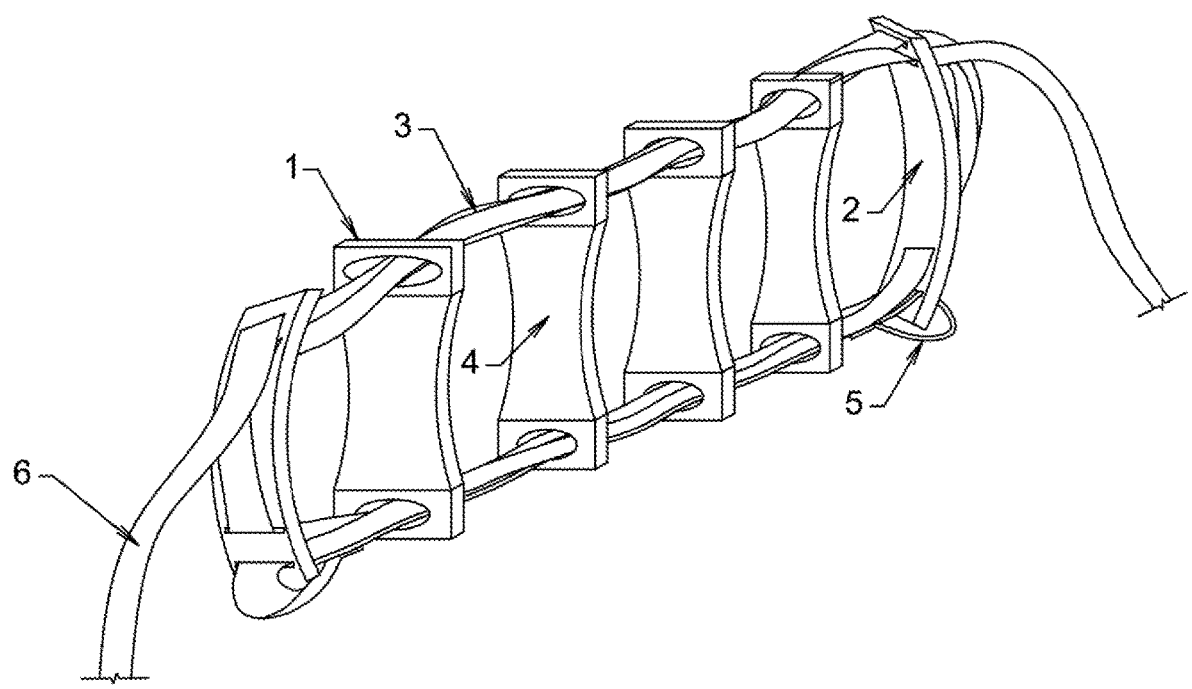
FIG. 4 is an isolated and detailed view of the forefoot-encompassing region of the device.
Figure 5:
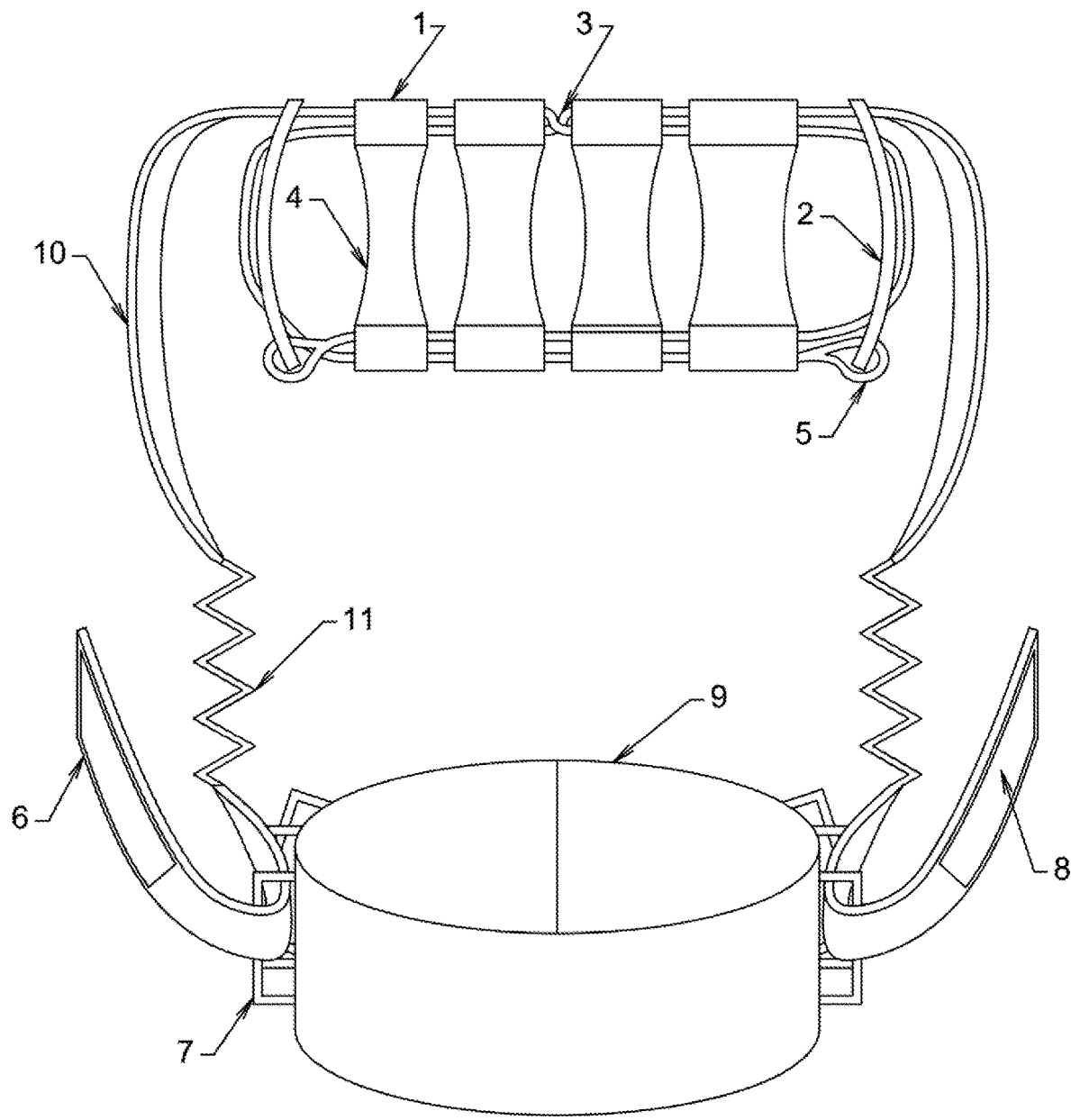
FIG. 5 is an alternative embodiment to FIG. 1, which includes an integrated elastic and stretchable element (11) and is configured for enabling the performance of plantar-flexion movements with resistance.

DETAILED DESCRIPTION OF THE INVENTION:

Continuous adjustment to the gaps between the inter-toe spacing elements (4) is enabled by the sliding action of the hollow connection slots (1) along the flexible rail straps (3).

An opposite orientation of the anchored ends (5) and the attached clasp mechanisms (2) creates a drawstring effect on the flexible rail straps (3), such that after (3) has been looped through the connection slots (1) of the inter toe spacing elements (4), an application of tensile force to the travelling ends (6) causes the single forefoot loops of the flexible rail straps (3) to tighten, thus securing the inter toe spacing elements (4) to the foot of a user.

Tension applied to the travelling ends (6) of the flexible rail straps (3) is set and maintained with the cuff which surrounds the lower leg (9) and its connected auxiliary attachment surfaces (7), where the connection between the travelling ends (6) of the flexible rail straps (3) and the attachment surfaces (7) on the cuff (9) comprise the inelastic tensile link (10) which creates dorsiflexion in the foot and lower leg. The secure connection between (6) and (7) can be made with Velcro, as shown with (8), while the use of cam buckles and other hardware variants for the attachment mechanism is obvious to one skilled in the art field of the present invention. The elastic and stretchable element (11) can be integrated with the flexible rail strap (3) at a location preceding its travelling end (6) and will provide a resistance mechanism when performing plantarflexion exercises.

The invention claimed is:

1. A device which stretches enables a musculoskeletal stretching of a human foot, comprised of:
   a) a plurality of inter-toe spacing elements of columnar form, each spacing element comprising dual vertical ends with integrated hollow connection slots, and being of sufficient length such that one vertical end extends above, and the other extends below, a forefoot plane;
   b) a pair of flexible rail straps, each of the rail straps comprising a piece of webbing with an anchored end and an opposite travelling end, where both of the travelling ends insert through each connection slot of every inter-toe spacing element in opposite directions, to form a closed loop around the forefoot plane;
   c) a pair of curved clasps, where each clasp features an attachment point for the anchored end of one flexible rail strap, and a plurality of insertion points through which both travelling ends of said flexible rail straps pass, and, d) a cuff configured to surround a lower leg region, and which features a plurality of auxiliary attachment surfaces, where said attachment surfaces connect with corresponding travelling ends of the flexible rail straps configured to create dual inelastic tensile force linkages between the forefoot plane and the lower leg region, said cuffs being of adjustable length, through a tensioning action of the rail straps between said attachment surfaces and the travelling end insertion points of the clasps.

2. device of claim 1, wherein an elastic and stretchable material element is integrated in series with the flexible rail straps, between the travelling end insertion points of the clasps and the cuff attachment surfaces, which is configured to enable a performance of foot plantarflexion exercises with resistance.

\* \* \* \* \*